(12) United States Patent
Hayashizaki et al.

(10) Patent No.: US 6,508,923 B1
(45) Date of Patent: Jan. 21, 2003

(54) MULTI-CAPILLARY ELECTROPHORETIC APPARATUS

(75) Inventors: Yoshihide Hayashizaki, Tsukuba (JP); Akira Harada, Kyoto (JP)

(73) Assignees: Shimadzu Corporation, Kyoto (JP); The Institute of Physical and Chemical Research, Saitama (JP)

( * ) Notice: Subject to any disclaimer, the term of this patent is extended or adjusted under 35 U.S.C. 154(b) by 0 days.

(21) Appl. No.: 09/566,976

(22) Filed: May 9, 2000

(30) Foreign Application Priority Data

May 12, 1999 (JP) .......................................... 11-130771

(51) Int. Cl.[7] ............................ C02F 1/40; C02F 11/00; C25B 11/00; C25B 13/00; G01N 27/27; G01N 27/403
(52) U.S. Cl. ........................ 204/603; 204/452; 204/252
(58) Field of Search ................................ 382/128, 129; 762/19, 20, 22, 25, 27, 72; 204/603, 452, 252; 356/344; 422/70

(56) References Cited

U.S. PATENT DOCUMENTS

| | | | | |
|---|---|---|---|---|
| 5,108,179 A | * | 4/1992 | Myers ...................... 250/459.1 |
| 5,324,401 A | * | 6/1994 | Yeung et al. ................ 204/452 |
| 5,582,705 A | * | 12/1996 | Yeung et al. ................ 204/452 |
| 5,741,411 A | | 4/1998 | Yeung et al. |
| 5,790,727 A | * | 8/1998 | Dhadwal et al. ............. 204/452 |
| 5,867,266 A | * | 2/1999 | Craighead ................... 204/450 |
| 5,903,348 A | * | 5/1999 | Melman et al. .............. 204/451 |
| 5,982,486 A | | 11/1999 | Wang |
| 6,017,765 A | * | 1/2000 | Yamada et al. ............. 204/602 |
| 6,043,882 A | | 3/2000 | De Wolf et al. |
| 6,048,444 A | * | 4/2000 | Takahashi et al. .......... 204/451 |
| 6,084,667 A | * | 7/2000 | Melman et al. ............. 356/246 |
| 6,120,667 A | * | 9/2000 | Hayashizaki et al. ....... 204/603 |
| 6,270,644 B1 | * | 8/2001 | Mathies et al. ............. 204/600 |

FOREIGN PATENT DOCUMENTS

JP 11183461 A * 7/1999 .......... G01N/30/74

OTHER PUBLICATIONS

Xiong, Shao–Xiang et al. "Studies on the coupling technique between high performance capillary electrophoresis and charge–coupled device detector. (III). Quantitative calculation methods", Gaodeng Xuexiao Huaxue Xuebao (1996), 17(1), 38–41.*

Heiger, D. "High Performance Capillary Electrophoresis— An Introduction", 3rd Ed. France, Hewlett Packard Company, (1997) 36–39, 79, 92–105.*

* cited by examiner

Primary Examiner—Jill Warden
Assistant Examiner—Jennine Brown
(74) Attorney, Agent, or Firm—Rader, Fishman & Grauer, PLLC (57) ABSTRACT

A data processing part comprises a time-series data production part for producing time-series data as to each capillary column from a scan waveform obtained by an optical measuring part, further comprises a correction data storage part for storing correction data indicating the relation between the number of data points of saturated parts and light intensity data obtained on the assumption that a peak is unsaturated as to a saturated scan waveform peak and a saturated data correction part obtaining light intensity data as to the saturated peak included in the scan waveform on the basis of the correction data stored in the correction data storage part, and employs the light intensity data obtained by the saturated data correction part as the time-series data.

15 Claims, 9 Drawing Sheets

Fig. 1

Fig. 2A
SCAN WAVEFORM

Fig. 2B
TIME-SERIES DATA

Fig. 6A
SCAN WAVEFORM  y(t)

Fig. 6B
THEORETIC WAVEFORM  x(t)

Fig. 6C
SUPERPOSE IMPULSE RESPONSE h(τ)

$$y(t) = \int_{-\infty}^{\infty} h(\tau) \cdot x(t-\tau) d\tau$$

SIMULATE BY y(t)

MULTI-CAPILLARY ELECTROPHORETIC APPARATUS

BACKGROUND OF THE INVENTION

1. Field of the Invention

The present invention relates to a multi-capillary electrophoretic apparatus employed for separation of protein or sequence determination for DNA.

2. Description of the Prior Art

A multi-capillary electrophoretic apparatus comprises a multi-capillary array electrophoresis part, an optical measuring part and a data processing part The multi-capillary array electrophoresis part has an arrangement of a plurality of capillary columns for injecting each of a plurality of samples into the capillary columns and simultaneously electrophoresing the same in all capillary columns. The optical measuring part irradiates the capillary columns with light in the multi-capillary array electrophoresis part, scans the irradiated positions perpendicularly to an electrophoresis direction, detects the intensity of light from the samples of the irradiated parts and measures scan waveforms. The data processing part produces time-series data as to each capillary column from the scan waveforms obtained by the optical measuring part.

A multi-capillary electrophoretic apparatus for sequence determination for DNA employs Sanger's reaction and electrophoreses a DNA fragment sample prepared by labeling a primer or a terminator with a fluorescent material for detecting fluorescence from the DNA fragment sample in the course of electrophoresis and determining the base sequence.

A high-speed DNA sequencer having high sensitivity and high throughput is necessary for sequence determination for DNA such as a human genome having long base sequence. For example, a multi-capillary DNA sequencer having an arrangement of a plurality of capillary columns charged with gels is proposed in place of that employing flat slab gels. With such capillary columns, samples are not only easy to handle or inject but can also be electrophoresed at a high speed and detected in high sensitivity as compared with the slab gels. While bands are spread due to influence by Joulean heat or a temperature gradient is caused when a high voltage is applied to the slab gels, the capillary columns have no such problem and enable high-speed detection with small spreading of bands in high-speed electrophoresis with application of a high voltage.

Figure 1:
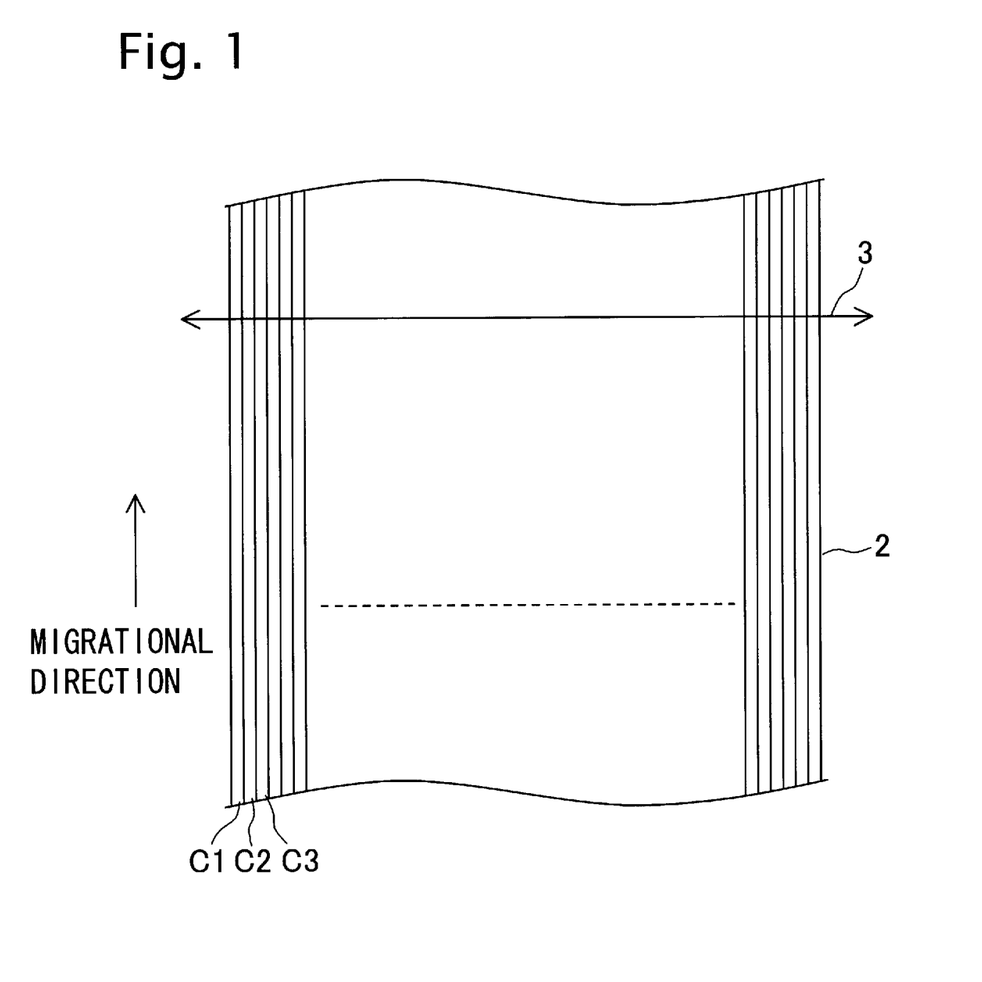
FIG. 1 schematically illustrates scanning in an online multi-capillary electrophoretic apparatus.

Upon measuring scan waveforms by an optical measuring part in an online multi-capillary electrophoretic apparatus, a detected part of a capillary array 2 having an alignment of a plurality of capillary columns is scanned perpendicularly to a direction for elecbtrophoresing samples in the capillary columns as shown by a straight line 3 in FIG. 1 for receiving fluorescence from the samples passing through the scanned position. The fluorescence is received at for example 13000 points, in a single scanning. Each of these points is referred to as a sampling point or a data point The samples, which are DNA fragment samples, are labeled in four types in response to end bases adenine (A), guanine (G), thymine (T) and cytosine (C). Therefore, the base sequence can be determined by separating the received fluorescence into its spectral components thereby identifying the types of the bases passing through the scanned position.

Figure 2A:
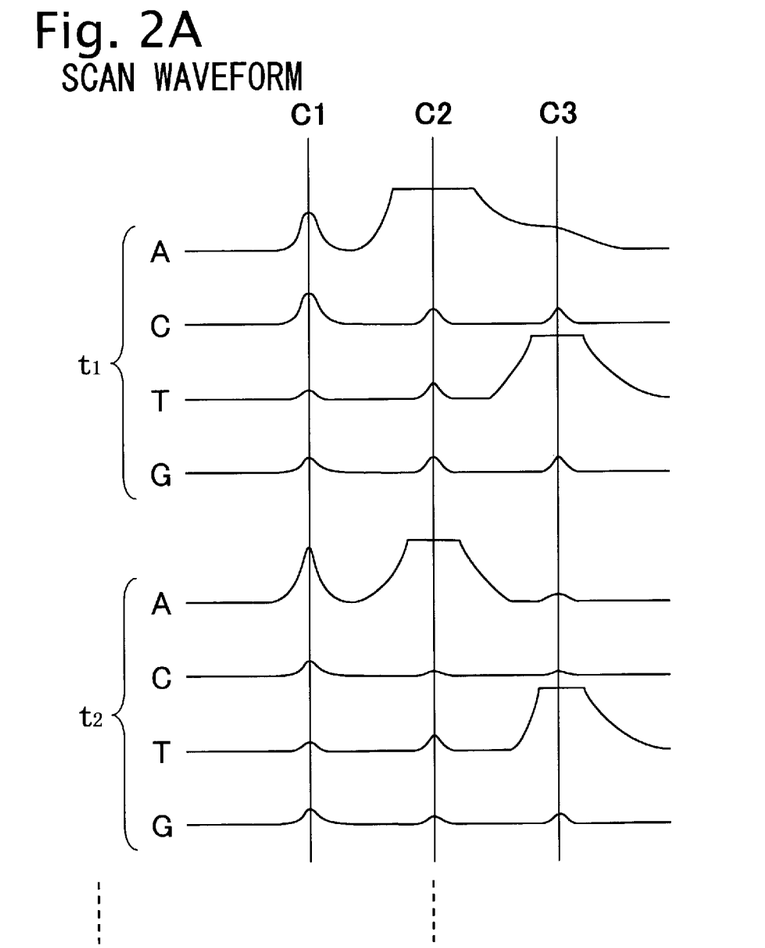
FIG. 2A illustrates scan waveforms in the online multi-capillary electrophoretic apparatus.

Scan waveforms obtained by scanning the scan line 3 on a fixed time frame are detected as peaks by electrophoresing and passing the DNA fragment samples through columns C1, C2, C3, . . . , as shown in FIG. 2A. While symbols A, C, T and G denote DNA fragments of the four types of bases respectively, a common detector detects these four signals as light components of different wavelengths. Symbols $t_1$, $t_2$, . . . denote times of scanning the scan line 3 respectively at a rate of once a second, for example.

Figure 2B:
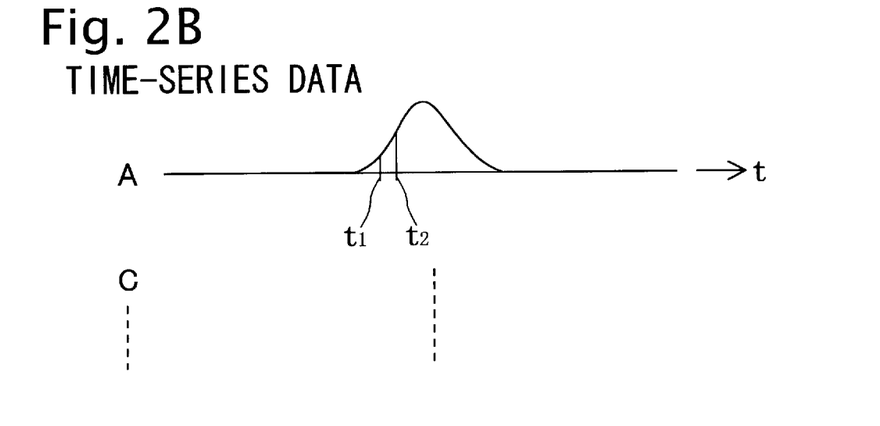
FIG. 2B illustrates time-series data produced therefrom.

The DNA fragment samples pass through the position of the scan line 3 and hence the scan waveforms change with the elapse of time. When arranging data on a prescribed position of each column from the scan waveforms for the respective end bases as to each column, time-series data shown in FIG. 2B is obtained. FIG. 2B shows part of time-series data related to adenine (A) as to the column C1.

In the scan waveforms obtained by scanning the scan line 3, there may exist such signals exceeding input levels as those of adenine (A) and thymine (T) in the columns C2 and C3 in FIG. 2A. The input levels are determined by the detection range of the detector of the optical measuring part or the input range of an A—D converter capturing data in a data processing part When detected signals exceed the input levels, the peaks on the scan waveforms are saturated. When producing time-series data from the scan waveforms including the saturated peaks, the time-series data are distorted.

Also, the scan waveforms have tailing due to an electric time-constant of the detector. Therefore, in the scan waveform of a capillary column detected immediately after a capillary column allowing detection of strong fluorescence, influence by tailing of the strong signal appears with addition of signal intensity. This also results in distortion.

When producing time-series data from scan waveforms, positions for acquiring the time-series data from the scan waveforms are previously fixed with reference to the positions of the capillary columns. However, fluctuation of peak positions may be observed also in scan waveforms in a short time so assumed that the capillary column positions hardly fluctuate. When acquiring the time-series data from the scan waveforms on the basis of previously set capillary column position information in this case, it follows that the data are acquired around non-peak positions in the capillary columns depending on scanning, also resulting in distortion.

Furthermore, the positions of the capillary columns may fluctuate with the elapse of time. Also in this case, it follows that the data are acquired on positions varied with time in the capillary columns when acquiring the time-series data from the scan waveforms on the basis of previously set capillary column position information, also resulting in distortion.

When the time-series data are distorted due to tailing or fluctuation of the positions of data acquisition, errors may be caused when determining the base sequence.

SUMMARY OF THE INVENTION

Accordingly, an object of the present invention is to improve the precision of time-series data by reducing distortion caused when converting scan waveforms to time-series data.

A multi-capillary electrophoretic apparatus according to the present invention comprises a multi-capillary array electrophoresis part having an arrangement of a plurality of capillary columns for injecting each of a plurality of samples into the capillary columns and simultaneously electrophoresing the samples in all capillary columns, an optical measuring part for measuring scan waveforms by irradiating the capillary columns with light in the multi-capillary array electrophoresis part, scanning irradiated positions in a direction perpendicular to a electrophoresis direction, and detecting the intensity of light from the samples of irradiated parts, and a data processing part for producing time-series data as to each capillary column from the scan waveforms obtained by the optical measuring part In order to reduce distortion caused in conversion to the time-series data, the data processing part comprises a saturated data correction part for correcting saturated peaks included in the scan waveforms, which are saturated beyond the detection range of a detector of the optical measuring part or the input range of an A—D converter capturing data in the data processing part, to light intensity value measured on the assumption that the peaks are unsaturated in an aspect of the present invention. The data processing part produces the time-series data on the basis of unsaturated scan waveform peaks and the light intensity value corrected by the saturated data correction part as to the saturated scan waveform peaks.

In order to correct saturated data, the data processing part preferably comprises a correction data storage part for storing correction data indicating the relationship between the number of data points of saturated parts of the saturated scan waveform peaks and light intensity data obtained on the assumption that the peaks are unsaturated. The saturated data correction part corrects measured light intensity value on the basis of the correction data stored in the correction data storage part as to the saturated peaks.

The correction data storage part can store correction data indicating the relationship between the number of the data points of the saturated parts and peak heights obtained on the assumption that the peaks are unsaturated. In this case, the saturated data correction part can employ the peak heights stored in the correction data storage part as time-series data of the saturated scan waveform peaks.

The correction data storage part can store correction data indicating the relationship between the number of the data points of the saturated parts and scan waveforms obtained on the assumption that the peaks are unsaturated. In this case, the saturated data correction part can employ the data on prescribed positions of the corrected scan waveforms of the capillary columns as time-series data of the saturated scan waveform peaks.

According to this aspect of the present invention, the saturated data correction part obtains the light intensity value measured on the assumption that the peaks are unsaturated for producing the time-series data with the corrected light intensity value, thereby suppressing distortion of the time-series data.

According to another aspect of the present invention, the data processing part comprises a tailing correction part for removing tailing components caused by electric time-constants of the light intensity signals of capillary columns located on front positions in the scan waveforms when producing the time-series data from the scan waveforms.

According to this aspect of the present invention, the time-series data can be obtained on the basis of correct signal intensity by removing influence by tailing.

According to yet another aspect of the present invention, the data processing part comprises a capillary position correction part for obtaining a position maximizing the light intensity signals around the previously set capillary column position for data acquisition, and acquires the time-series data on the basis of the position maximizing the light intensity signals obtained by the capillary position correction part when producing the time-series data from the scan waveforms.

According to a further aspect of the present invention, the data processing part has a function of periodically correcting the capillary column position information for data acquisition, and acquires the time-series data from the scan waveforms on the basis of the corrected capillary column position information when producing the time-series data from the scan waveforms.

Thus, distortion of the time-series data resulting from errors in the positions for acquiring the time-series data can be prevented by correcting the positions for acquiring the time-series data from the scan waveforms.

The multi-capillary electrophoretic apparatus may comprise any one or more than two of the saturated data correction part, the tailing correction part, the capillary position correction part having the function of obtaining the position maximizing the light intensity signal and the capillary position correction part having the function of periodically correcting the capillary column position information.

The correction data storage part can store the correction data indicating the relationship between the number of the data points of the saturated parts and the peak heights obtained on the assumption that the peaks are unsaturated so that the saturated data correction part can employ the peak heights stored in the correction data storage part as time-series data of the saturated scan waveform peaks.

The correction data storage part can also store correction data indicating the relationship between the number of the data points of the saturated parts and scan waveforms obtained on the assumption that the peaks are unsaturated so that the saturated data correction part can employ data on prescribed positions of corrected scan waveforms of the capillary columns as time-series data of the saturated scan waveform peaks.

The multi-capillary electrophoretic apparatus according to the present invention correcting the light intensity data of the saturated peaks included in the scan waveforms, removing the tailing components or correcting the capillary position information for acquiring data can suppress distortion of the time-series data.

The foregoing and other objects, features, aspects and advantages of the present invention will become more apparent from the following detailed description of the present invention when taken in conjunction with the accompanying drawing.

DESCRIPTION OF THE PREFERRED EMBODIMENTS

Figure 3:
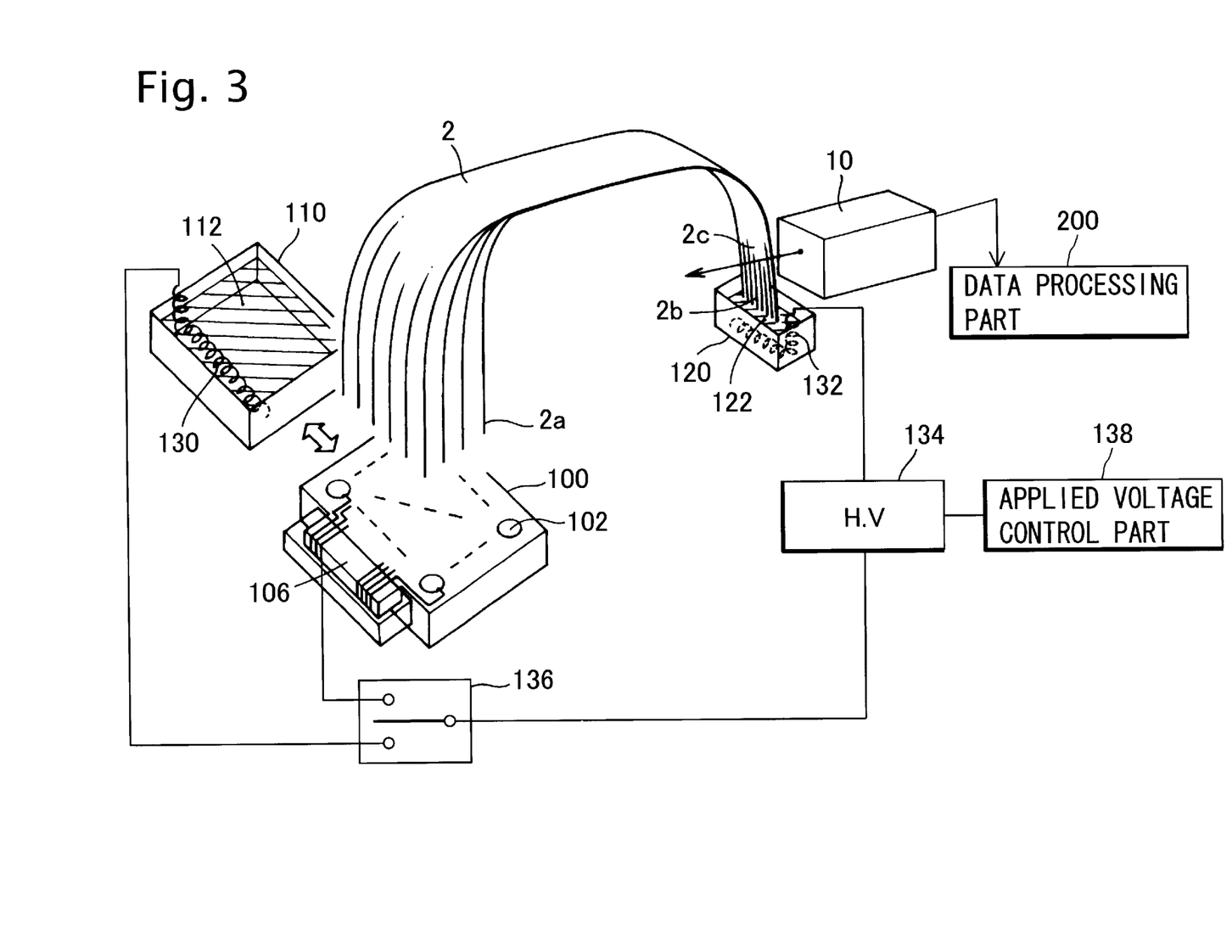
FIG. 3 is a schematic perspective view showing an embodiment.

FIG. 3 is a schematic perspective view showing an embodiment

A pair of reservoirs 110 and 120 store buffer solutions 112 and 122 with electrodes 130 and 132 provided therein respectively. A sample plate 100 made of an insulating material has a flat surface and a connector part 106 connected thereto. A plurality of wells 102 are vertically and horizontally arranged at regular intervals on the surface of the sample plate 100. Each well 102, which is a bottomed hole, is formed with an individual electrode pattern extending from the bottom to the connector part 106 through the surface of the sample plate 100. Samples are introduced into the respective wells 102 of the sample plate 100, and a high-voltage distribution cable is connected to the connector part 106.

The reservoir 110 and the sample plate 100 are switchably connected to a high-voltage switching part 136 so that distribution is switchable. A high-voltage power source 134 is connected between the high-voltage switching part 136 and the electrode 132 provided in the other reservoir 120. An applied voltage control part 138 controlling applied voltages and times for sample introduction and electrophoresis is connected to the high-voltage power source 134. A microcomputer or the like implements the applied voltage control part 138.

In sample injection, one ends 2a of capillary columns forming a capillary array 2 are inserted into the respective wells 102 of the sample plate 100. After sample injection, the one ends 2a of the capillary columns are dipped in the buffer solution 112 stored in the reservoir 110. Other ends 2b of the capillary columns forming the capillary array 2 are dipped in the buffer solution 122 stored in the reservoir 120. The capillary array 2 is provided with a detected part 2c on the side closer to the ends 2b, so that an optical measuring part 10 detecting the samples irradiates the detected part 2c with measuring light or excitation light for detecting absorbance by the samples or fluorescence from the samples. The optical measuring part 10 is connected to a data processing part 200 for converting scan waveforms obtained by the optical measuring part 10 to time-series data as to the respective capillary columns.

Figure 4:
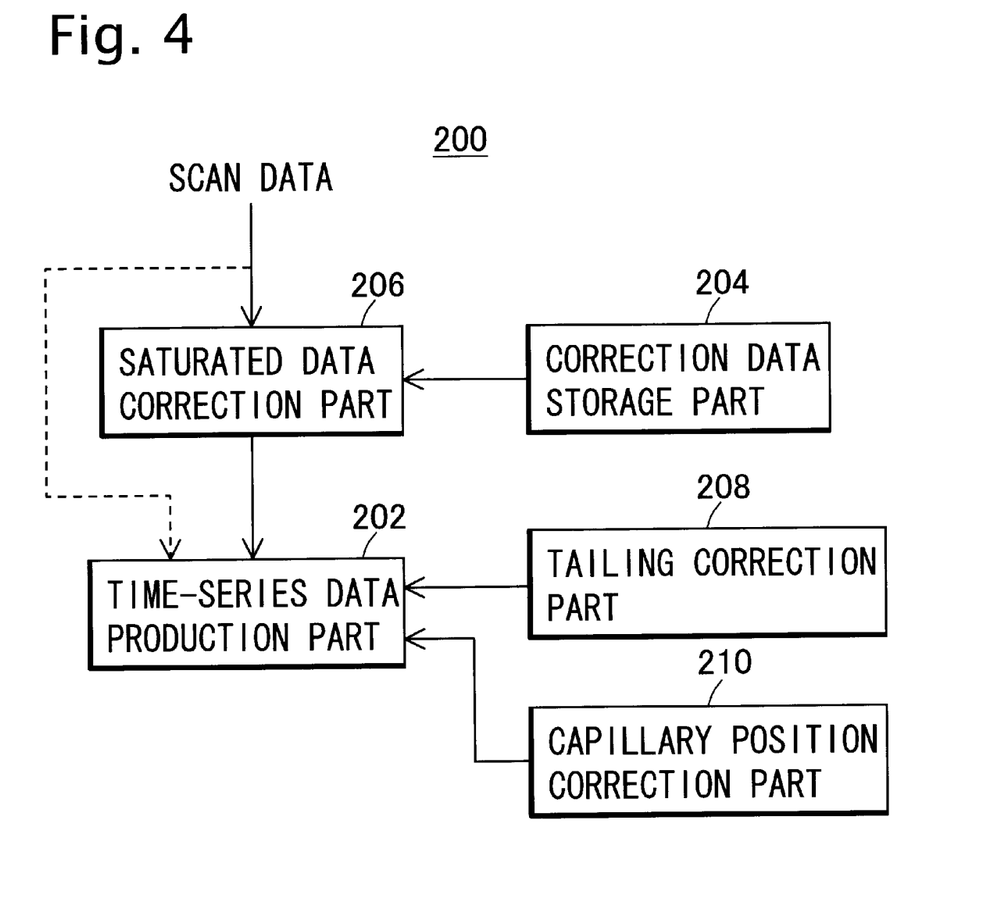
FIG. 4 is a block diagram showing a data processing part in the embodiment.

As shown in FIG. 4, the data processing part 200 comprises a time-series data production part 202 for producing the time-series data as to the respective capillary columns from the scan waveforms obtained by the optical measuring part 10.

Symbol 204 denotes a correction data storage part storing correction data indicating the relationship between the number of data points of saturated parts and light intensity data obtained on the assumption that peaks are unsaturated as to peaks saturated beyond the detection range of a detector of the optical measuring part 10 or the input range of an A–D converter capturing data in the data processing part 200 among peaks of the scan waveforms. Numeral 206 denotes a saturated data correction part for obtaining light intensity data as to the saturated peaks among the peaks of the scan waveforms on the basis of the correction data stored in the correction data storage part 204. The time-series data production-part 202 employs unsaturated scan waveform peaks as such while employing the light intensity data obtained by the saturated data correction part 206 as to saturated scan waveform peaks for producing the time-series data.

Numeral 208 denotes a tailing correction part removing tailing components caused by electric time-constants of light intensity signals from capillary columns located on front positions of the scan waveforms when the time-series data production part 202 produces the time-series data from the scan waveforms.

Numeral 210 denotes a capillary position correction part obtaining positions maximizing the light intensity signals around the previously set capillary column positions for data acquisition. When producing the time-series data from the scan waveforms, the time-series data production part 202 employs data of the positions obtained by the capillary position correction part 210 as the time-series data.

The capillary position correction part 210 can have a function of periodically correcting the capillary column position information for data acquisition. In this case, the time-series data production part 202 can acquire the time-series data from the scan waveforms on the basis of the corrected capillary column position information when producing the time-series data from the scan waveforms.

The capillary position correction part 210 may attain both or one of the functions of obtaining the positions maximizing the light intensity signals and the functions of periodically correcting the capillary column position information for data acquisition.

The data processing part 200 comprises the time-series data production part 202 as an indispensable one, and additionally comprises at least one the set of the correction data storage part 204 and the saturated data correction part 206, the tailing correction part 208 and the capillary position correction part 210. A broken line appearing in FIG. 4 shows connection in the case of not comprising the set made of the correction data storage part 204 and the saturated data correction part 206.

Referring again to FIG. 3, the capillary array 2 has a two-dimensional capillary column arrangement corresponding to the arrangement of the wells 102 of the sample plate 100 on the side of the one ends 2a. The capillary columns are aligned on the detected part 2c and irradiated with the measuring light or the excitation light from a direction perpendicular to the arrangement planes of the capillary columns.

The capillary columns, made of quartz glass or borosilicate glass (e.g., Pyrex), are for example 200 to 300 $\mu$m in outer diameter and 75 to 100 $\mu$m in inner diameter. The outer peripheries of the capillary columns are preferably covered with coatings of a non-fluorescent material such as $SiO_2$ not fluorescing by excitation light ranging from the ultraviolet region to the near-infrared region or fluorescing to a degree not hindering fluorescence measurement In this case, the coatings may not be removed on the detected part 2c. When the capillary columns have fluorescing resin coatings, the coatings are removed on the detected part 2c. A plurality of such capillary columns are arranged in the capillary array 2.

The capillary columns are charged with polyacrylamide gels, linear acrylamide gels, polyethylene oxide (PEO) gels or the like as gels of separation media. Samples containing four types of DNA fragments labeled with four types of fluorescent materials selected from fluorescent materials such as FAM, JOE, TAMRA, ROX, R6G and R-110 varied with end bases or labeled in four types with at least two types of fluorescent materials at different rates are injected into the capillary columns respectively and simultaneously electrophoresed.

A moving mechanism (not shown in FIG. 3) switches and arranges the sample plate 100 and the reservoir 110 as shown by thick arrow so that either one selectively comes into contact with the one ends 2a of the capillary columns.

Operations of this embodiment shall now be described.

The samples are introduced into the wells 102 of the sample plate 100 respectively. Aside from pre-treated samples being injected into the wells 102, the wells 102 can also be employed to perform sample injection by inserting capillary column ends into the samples introduced into the wells 102 after treating the samples by a PCR (polymerase chain reaction) method with the wells 102. The PCR method is a method of remarkably amplifying only the target part of DNA. With the PCR method, a primer is added to a sample of DNA and temperature is raised for dissociating double-stranded DNA to single chains. Then the temperature is lowered for bonding the primer to the DNA chains and the temperature is slightly raised for synthesizing DNA. The temperature is further raised for making single chains. The operation of lowering and raising the temperature is repeated for largely amplifying prescribed part of DNA.

After the samples are introduced into the wells 102, the one ends 2a of the capillary columns are respectively dipped into the samples stored in the wells 102 of the sample plate 100, and the other ends 2b of the capillary columns are collectively dipped in the buffer solution 122 stored in the reservoir 120. Through the high-voltage switching part 136, the wells 102 are connected to the high-voltage power source 134 through the connector part 106 and the electrode patterns 130 and 132.

The high-voltage power source 134 applies a high voltage between the wells 102 and the buffer solution 122 for injecting the samples into the capillary columns. The applied voltage control part 138 controls the voltage and the time to be applied.

After sample injection, the moving mechanism moves the sample plate 100 and the reservoir 110 thereby dipping the ends 2a of the capillary columns in the buffer solution 112 stored in the reservoir 110. Thereafter a high voltage is applied between the reservoirs 110 and 120 for performing separation by electrophoresis. A power supply voltage for electrophoresis is for example 30 kV, and a current capacity is 10 to 30 mA.

Operations of the data processing part 200 producing time-series data from scan waveforms shall now be described.

First, the relationship between the number of saturated data points (number of sampling points) and light intensity data (scan waveforms) are obtained on the assumption that peaks are unsaturated, and are stored in the correction data storage part 204 as a table or functions.

Figure 5:
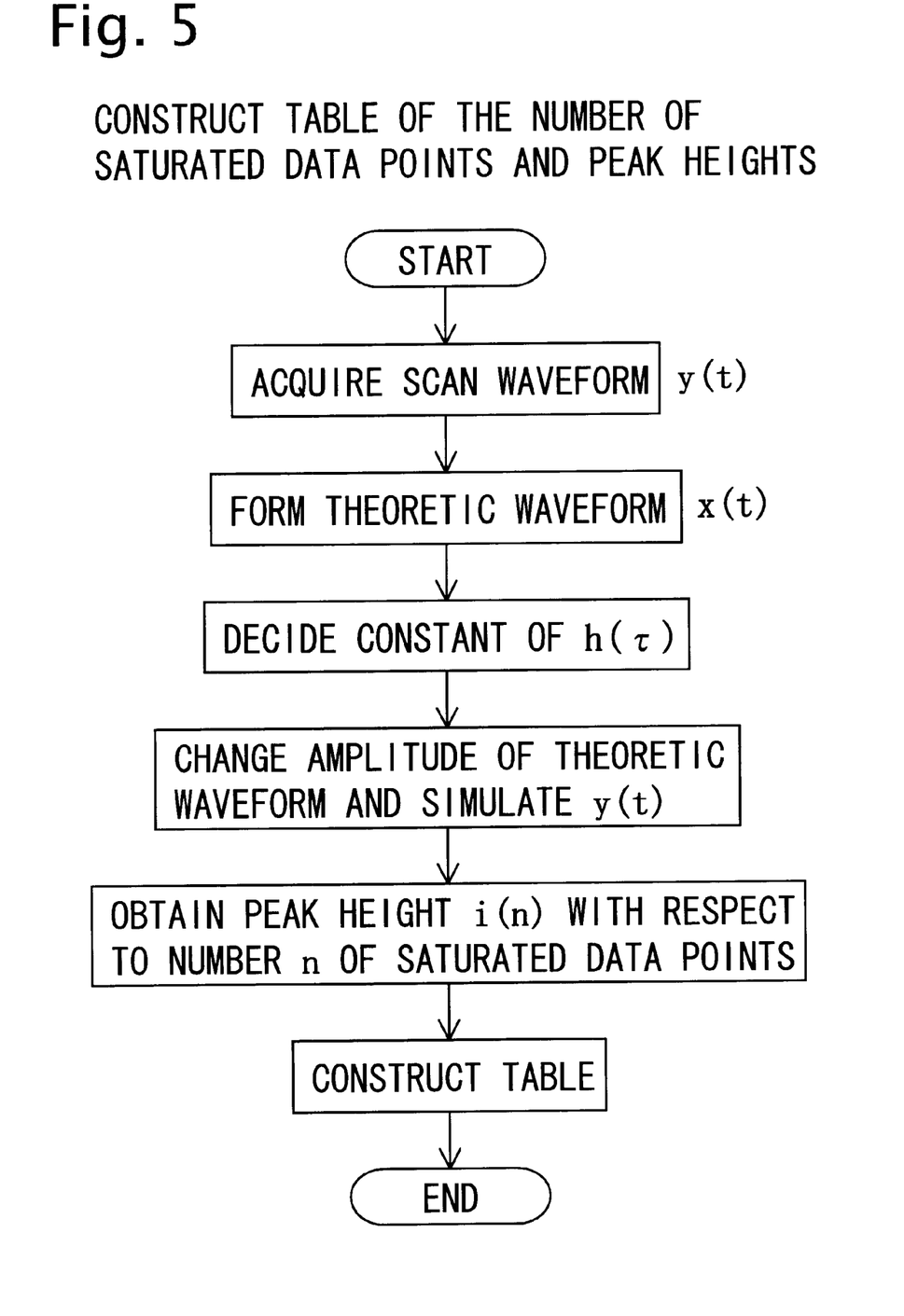
FIG. 5 is a flow chart showing a method of producing correction data.

A method of producing correction data is described with reference to a flow chart of FIG. 5 and waveform diagrams of FIGS. 6A to 6D.

An actual scan waveform (FIG. 6A) is acquired and a waveform as to a single capillary column is assumed to be y(t), where t represents time.

Figure 6A:
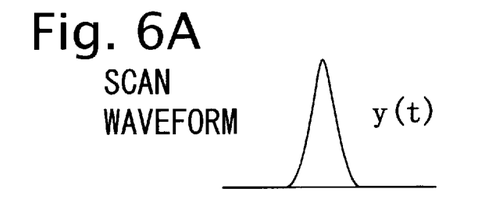
FIGS. 6A to 6D are waveform diagrams showing the method of producing the correction data.
Figure 6B:
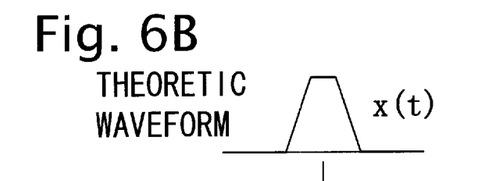

Then, a theoretical electrophoresis waveform x(t) (FIG. 6B) is formed. Assuming that h(t) represents a function indicating a characteristic specific to the apparatus, the actually observed output waveform y(t) is expressed as follows:

$$y(t) = \int_{-\infty}^{\infty} h(\tau) \cdot x(t-\tau) d\tau \quad (1)$$

Figure 6C:
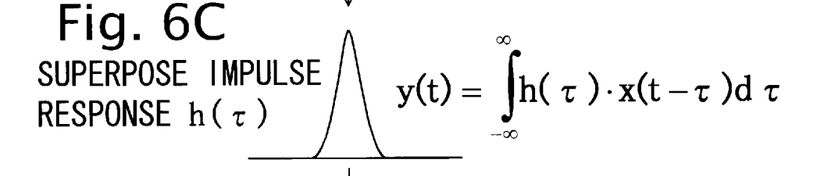

Assuming that h(τ) represents an impulse response, the following expression can be given (FIG. 6C):

$$h(t) = \frac{E}{\sqrt{\left(\frac{R}{2}\right)^2 - \frac{L}{C}}} \varepsilon^{-\alpha t} \sinh \gamma t \quad (2)$$

$$\alpha = \frac{R}{2L}$$

$$\gamma = \sqrt{\left(\frac{R}{2L}\right)^2 - \frac{1}{LC}}$$

The constant of the function h(t) can be obtained by fitting the above expression (1) to the actually acquired scan waveform.

Figure 6D:
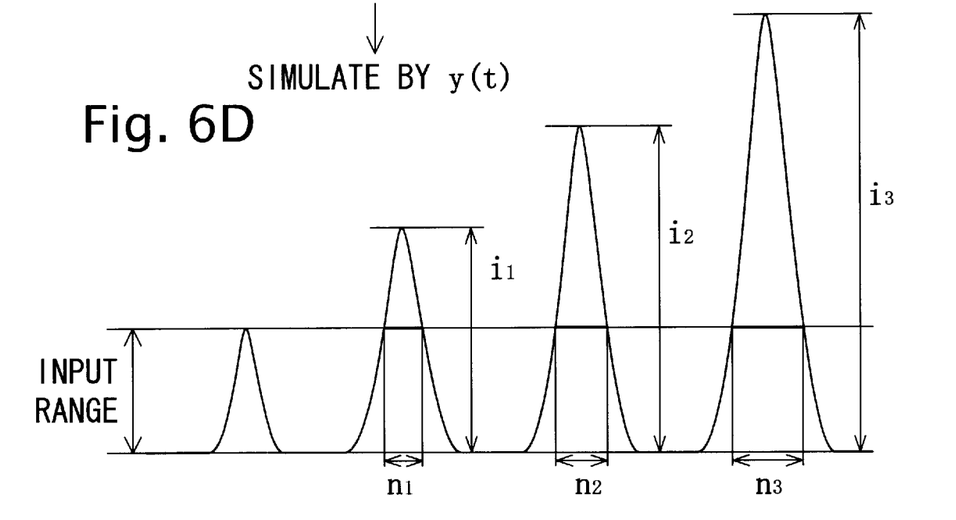
Figure 7:
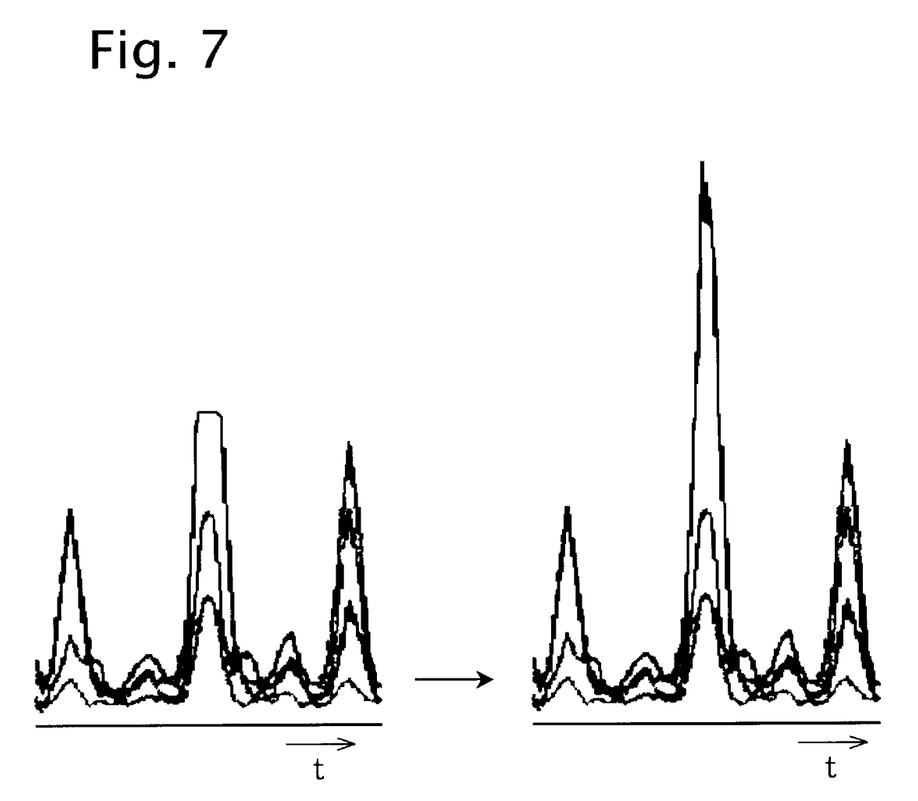
FIG. 7 is a waveform diagram partially showing time-series data obtained without correcting saturated data on the left side and data obtained with correction according to the present invention on the right side.

The waveform y(t) obtained by changing the amplitude of the theoretical waveform x(t) is simulated by the expression (1) with the function h(τ) whose constant is obtained, for obtaining the number n ($n_1$, $n_2$, $n_3$, . . . ) of data points (sampling points) saturated beyond the input range and peak heights i(n) ($i_1$, $i_2$, $i_3$, . . . ) on the assumption that peaks are unsaturated (FIG. 6D). The correction data storage part 204 stores these as a table or functions of i(n).

i(n) may be formed by not only the peak heights as those in this embodiment, but also by data on the respective sampling points on the assumption that the peaks are unsaturated, i.e., corrected scan waveform data. FIG. 7 shows part of time-series data in this case with superposition of four time-series data corresponding to the four types of end bases. The left-side data are obtained without correcting saturated data while the right-side data are obtained with correction by the present invention. A central saturated peak is corrected to a normal peak.

Figure 8:
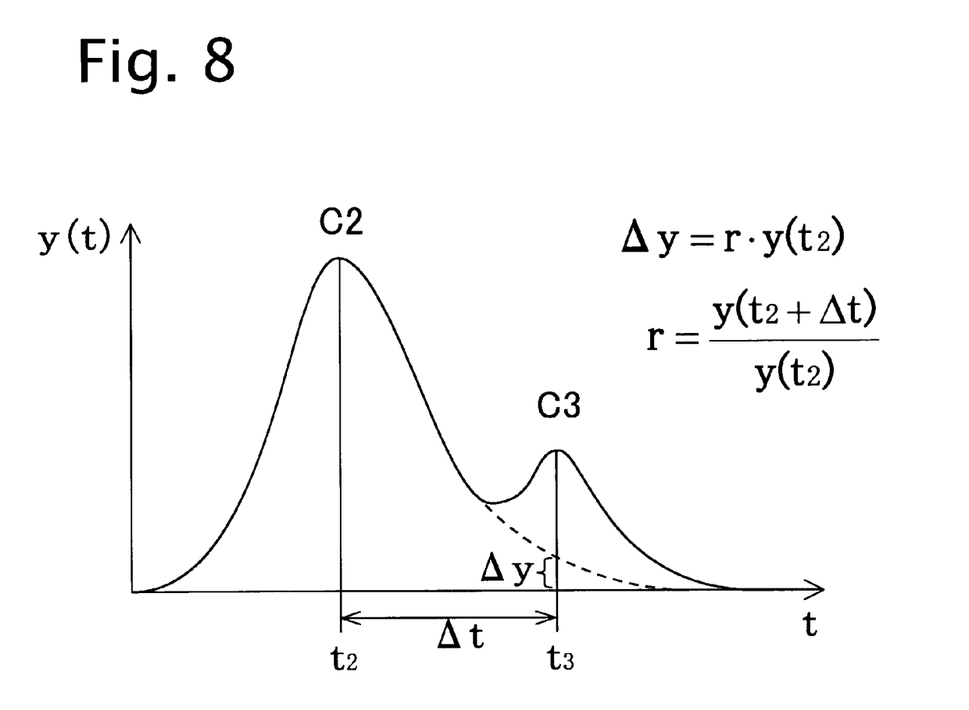
FIG. 8 is a waveform diagram showing a tailing correction method.

Tailing correction shall now be described. As shown in FIG. 8, it is assumed that a detection signal in a second capillary column is large in a scan waveform and this reaches a third peak, for example. The magnitude AΔ of the tailing can be obtained with a parameter of a capillary column interval AΔ (corresponds to the interval although expressed in time) as a signal component on a peak position of a capillary column temporally appearing next in the scan waveform from the output waveform y(t) formed with the previously obtained function h(τ). The magnitude Δy of the tailing is expressed as follows:

Δy=r·y where "y" represents the peak height y($t_2$) of the scan waveform in the column C2 and "r" represents the ratio of the signal in the column C2 on a peak position of the scan waveform of the next column C3, which can be expressed as follows:

Δr=($t_2$+Δt)/y($t_2$)

The magnitude Δy of the tailing caused by the signal of the column C2 is obtained on each sampling point of the peak of the column C3 and subtracted from a detection signal on each sampling point of the column C3 for correcting the peak of the scan waveform, and data on a prescribed position is collected as time-series data.

Figure 9:
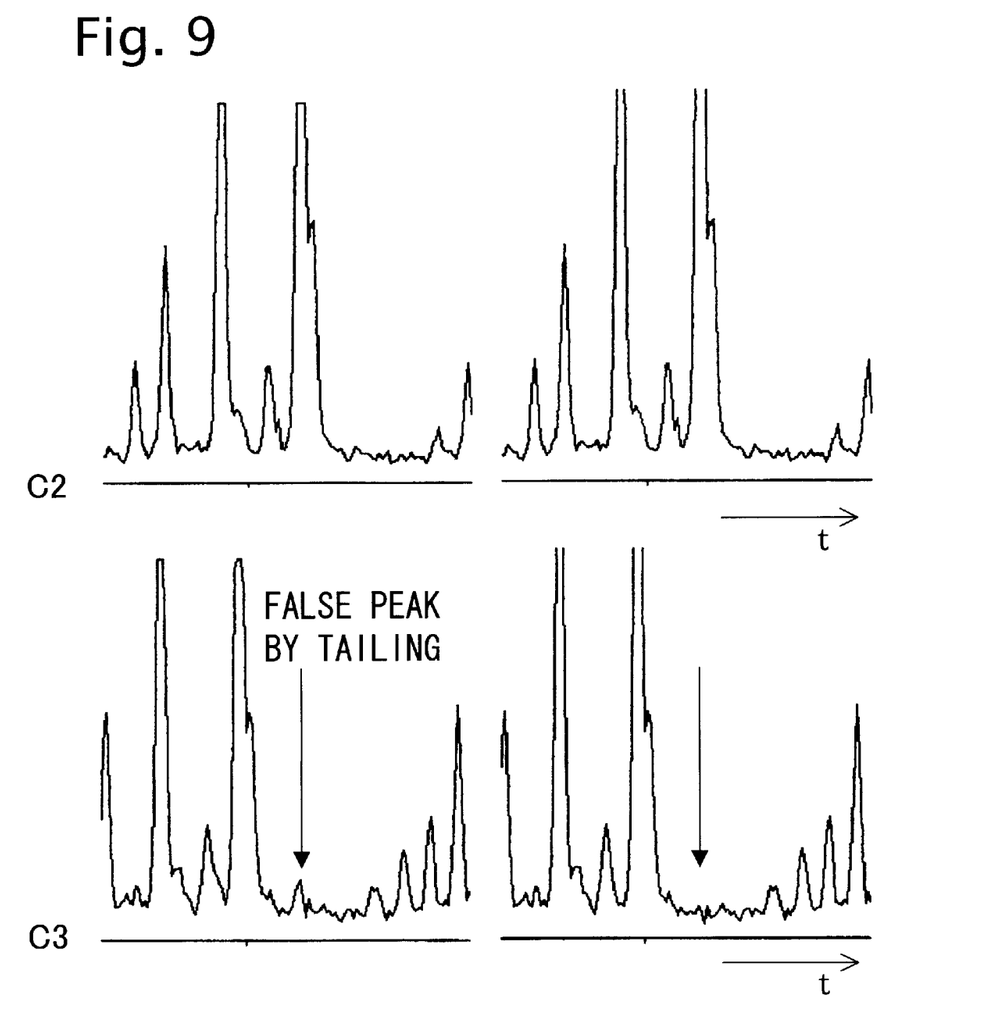
FIG. 9 shows time-series data influenced by tailing obtained without performing tailing correction on the left side and obtained with tailing correction according to the present invention on the right side.

FIG. 9 shows time-series data in the second capillary column and the third capillary column scanned immediately after the same. The left-side data are obtained without correcting tailing, and a peak influenced by tailing of a second large signal appears on a position of the third column shown by arrow. This false peak can be removed by performing tailing correction as shown on the right side.

When producing time-series data from scan waveforms, positions (sampling points) maximizing light intensity signals around the previously set capillary column positions for data acquisition are obtained. While it is possible to employ the data on the sampling points as the time-series data, simple addition mean values of data on several points around the sampling points were employed as the time-series data here.

The previously set capillary column positions for data acquisition were corrected every 500th scanning.

When correcting saturated peaks included in the scan waveforms to light intensity data obtained on the assumption that the peaks are unsaturated in response to the number of data points of saturated parts as in the embodiment, distortion of the time-series data can be suppressed.

By searching for points maximizing peaks in the capillary columns at every scanning and employing data around the same, the time-series data can be produced on the basis of correct capillary column position information also when the capillary column positions fluctuate at every scanning. Also by periodically correcting the capillary column position information, the time-series data can be produced on the basis of correct capillary column position information also when the capillary columns gradually move during electrophoresis.

In addition, the time-series data can be more correctly obtained by removing tailing components between adjacent capillary columns.

Although the present invention has been described and illustrated in detail, it is clearly understood that the same is by way of illustration and example only and is not to be taken by way of limitation as the spirit and scope of the present invention are limited only by the terms of the appended claims.

What is claimed is:

1. A multi-capillary electrophoretic apparatus comprising:
   a multi-capillary array electrophoresis part having an arrangement of a plurality of capillary columns for injecting each of a plurality of samples into said capillary columns and simultaneously electrophoresing said samples in all said capillary columns;
   an optical measuring part for measuring scan waveforms by irradiating said capillary columns with light in said multi-capillary array electrophoresis part, scanning irradiated positions in a direction perpendicular to an electrophoresis direction, and detecting the intensity of light from said samples of irradiated parts; and
   a data processing part for producing time-series data as to each said capillary column from said scan waveforms obtained by said optical measuring part, wherein
   said data processing part comprises a saturated data correction part for correcting saturated peaks included in said scan waveforms to light intensity value measured on the assumption that said peaks are unsaturated, and produces said time-series data on the basis of unsaturated scan waveform peaks with no correction and light intensity value of saturated scan said data processing part further comprises a capillary position correction part for periodically correcting capillary column position information for data acquisition and acquiring said time-series data from said scan waveforms on the basis of corrected capillary column position information when producing said time-series data from said scan waveforms.

2. The multi-capillary electrophoretic apparatus according to claim 1, wherein
   said data processing part comprises a correction data storage part for storing correction data indicating the relationship between the number of data points of saturated parts of said saturated peaks and light intensity data obtained on the assumption that said peaks are unsaturated, and
   said saturated data correction part corrects measured light intensity value on the basis of said correction data stored in said correction data storage part as to said saturated peaks.

3. The multi-capillary electrophoretic apparatus according to claim 2, wherein
   said correction data storage part stores correction data indicating the relationship between the number of said data points of said saturated parts and peak heights obtained on the assumption that said peaks are unsaturated, and
   said saturated data correction part employs said peak heights stored in said correction data storage part as time-series data of said saturated peaks.

4. The multi-capillary electrophoretic apparatus according to claim 2, wherein
   said correction data storage part stores correction data indicating the relationship between the number of said data points of said saturated parts and scan waveforms obtained on the assumption that said peaks are unsaturated, and
   said data processing part employs data on prescribed positions of corrected scan waveforms of said capillary columns as time-series data of said saturated scan waveform peaks.

5. The multi-capillary electrophoretic apparatus according to claim 1, wherein
   said data processing part further comprises a tailing correction part for removing tailing components caused by electric time-constants of light intensity signals of capillary columns located on front positions in said scan waveforms when producing said time-series data from said scan waveforms.

6. The multi-capillary electrophoretic apparatus according to claim 5, wherein
   said data processing part further comprises a first capillary position correction part for obtaining positions maximizing said light intensity signals around the previously set capillary column positions for data acquisition and acquires said time-series data on the basis of said positions maximizing said light intensity signals obtained by said first capillary position correction part when producing said time-series data from said scan waveforms.

7. The multi-capillary electrophoretic apparatus according to claim 6, wherein
   said data processing part further comprises a second capillary position correction part for periodically correcting said capillary column position information for data acquisition and acquires said time-series data from said scan waveforms on the basis of said corrected capillary column position information when producing said time-series data from said scan waveforms.

8. The multi-capillary electrophoretic apparatus according to claim 1, wherein
   said data processing part further comprises a first capillary position correction part for obtaining positions maximizing said light intensity signals around the previously set capillary column positions for data acquisition and acquires said time-series data on the basis of said positions maximizing said light intensity signals obtained by said first capillary position correction part when producing said time-series data from said scan waveforms.

9. The multi-capillary electrophoretic apparatus according to claim 8, wherein said data processing part further comprises a second capillary position correction part for periodically correcting said capillary column position information for data acquisition and acquires said time-series data from said scan waveforms on the basis of corrected said capillary column position information when producing said time-series data from said scan waveforms.

10. A multi-capillary electrophoretic apparatus comprising:

a multi-capillary array electrophoresis part having an arrangement of a plurality of capillary columns for injecting each of a plurality of samples into said capillary columns and simultaneously electrophoresing said samples in all said capillary columns;

an optical measuring part for measuring scan waveforms by irradiating said capillary columns with light in said multi-capillary array electrophoresis part, scanning irradiated positions in a direction perpendicular to an electrophoresis direction, and detecting the intensity of light from said samples of irradiated parts; and a data processing part for producing time-series data as to each said capillary column from said scan waveforms obtained by said optical measuring part, wherein said data processing part comprises a tailing correction part for removing tailing components caused by electric time-constants of light intensity signals of capillary columns located on front positions in said scan said data processing part further comprises a capillary position correction part for periodically correcting capillary column position information for data acquisition and acquiring said time-series data from said scan waveforms on the basis of corrected capillary column position information when producing said time-series data from scan waveforms.

11. The multi-capillary electrophoretic apparatus according to claim 10, wherein said data processing part further comprises a first capillary position correction part for obtaining positions maximizing said light intensity signals around the previously set capillary column positions for data acquisition and acquires said time-series data on the basis of said positions maximizing said light intensity signals obtained by said first capillary position correction part when producing said time-series data from said scan waveforms.

12. The multi-capillary electrophoretic apparatus according to claim 11, wherein said data processing part further comprises a second capillary position correction part for periodically correcting said capillary column position information for data acquisition and acquires said time-series data from said scan waveforms on the basis of corrected said capillary column position information when producing said time-series data from said scan waveforms.

13. A multi-capillary electrophoretic apparatus comprising;

a multi-capillary array electrophoresis part having an arrangement of a plurality of capillary columns for injecting each of a plurality of samples into said capillary columns and simultaneously electrophoresing said samples in all said capillary columns;

an optical measuring part for measuring scan waveforms by irradiating said capillary columns with light in said multi-capillary array electrophoresis part, scanning irradiated positions in a direction perpendicular to an electrophoresis direction, and detecting the intensity of light from said samples of irradiated parts; and a data processing part for producing time-series data as to each said capillary column from said scan waveforms obtained by said optical measuring part, wherein said data processing part comprises a first capillary position correction part for obtaining positions maximizing light intensity signals around the previously set capillary column position information for data acquisition for acquiring said time-series data on the basis of said positions maximizing said light intensity signals obtained by said first capillary position correction part when producing said time-series data from said scan waveforms.

14. The multi-capillary electrophoretic apparatus according to claim 13, wherein said data processing part further comprises a second capillary position correction part for periodically correcting said capillary column position information for data acquisition and acquires said time-series data from said scan waveforms on the basis of corrected said capillary column position information when producing said time-series data from said scan waveforms.

15. A multi-capillary electrophoretic apparatus comprising:

multi-capillary array electrophoresis part having an arrangement of a plurality of capillary columns for injecting each of a plurality of samples into said capillary columns and simultaneously electrophoresing said samples in all said capillary columns;

an optical measuring part for measuring scan waveforms by irradiating said capillary columns with light in said multi-capillary array electrophoresis part, scanning irradiated positions in a direction perpendicular to an electrophoresis direction, and detecting the intensity of light from said samples of irradiated parts; and a data processing part for producing time-series data as to each said capillary column from said scan waveforms obtained by said optical measuring part, wherein said data processing part further comprises a capillary position correction part for periodically correcting capillary column position information for data acquisition and acquires said time-series data from said scan waveforms on the basis of corrected said capillary column position information when producing said time-series data from said scan waveforms.

* * * * *

UNITED STATES PATENT AND TRADEMARK OFFICE
CERTIFICATE OF CORRECTION

PATENT NO. : 6,508,923 B1  Page 1 of 1
DATED : January 21, 2003
INVENTOR(S) : Yoshihide Hayashizaki et al.

It is certified that error appears in the above-identified patent and that said Letters Patent is hereby corrected as shown below:

<u>Title page,</u>
Item [73], the assignees should read:
-- [73] Assignees: Shimadzu Corporation, Kyoto, Japan
The Institute to Physical and Chemical Research, Saitama, Japan
Japan Science and Technology Corporation, Saitama, Japan --

Signed and Sealed this

Fifteenth Day of April, 2003

JAMES E. ROGAN
*Director of the United States Patent and Trademark Office*